(12) United States Patent
Saviano et al.

(10) Patent No.: US 7,329,644 B2
(45) Date of Patent: Feb. 12, 2008

(54) PREPARATION AND USE OF CYCLIC AND BRANCHED PEPTIDES AND THEIR LABELLED DERIVATIVES AS THERAPEUTIC AGENTS, CHOLECYSTOKININ AGONISTS OR ANTAGONISTS, AND DIAGNOSTIC AGENTS TO IDENTIFY AND LOCATE TUMOURS

(75) Inventors: Michele Saviano, Milan (IT); Stefania De Luca, Milan (IT); Giancarlo Morelli, Milan (IT); Diego Tesauro, Milan (IT); Carlo Pedone, Milan (IT)

(73) Assignee: Bracco Imaging S.p.A., Milan (IT)

( * ) Notice: Subject to any disclaimer, the term of this patent is extended or adjusted under 35 U.S.C. 154(b) by 188 days.

(21) Appl. No.: 10/479,096

(22) PCT Filed: May 21, 2002

(86) PCT No.: PCT/EP02/05562

§ 371 (c)(1),
(2), (4) Date: Jul. 16, 2004

(87) PCT Pub. No.: WO02/094873

PCT Pub. Date: Nov. 28, 2002

(65) Prior Publication Data

US 2004/0254339 A1 Dec. 16, 2004

(30) Foreign Application Priority Data

May 22, 2001 (IT) .......................... MI2001A1057

(51) Int. Cl.
A61K 38/00 (2006.01)
(52) U.S. Cl. .......................................................... 514/9
(58) Field of Classification Search .................... None
See application file for complete search history.

(56) References Cited

FOREIGN PATENT DOCUMENTS

| DE | 276482 | 10/1988 |
|----|--------|---------|
| EP | 0960939 | 1/1999 |
| WO | WO92/18627 | 10/1992 |
| WO | WO97/44341 | 11/1997 |

OTHER PUBLICATIONS

Robert T. Jensen, "Involvement of Cholecystokinin/Gastrin-Related Peptides and their Receptors in Clinical Gastrointestinal Disorders," Pharmacology & Toxicology, vol. 91, p. 333.*
Rudinger (J. Rudinger. In: Peptide Hormones, JA Parsons, Ed. (1976) 1-7).*
Sigma (Sigma. Designing Custom Peptides. http://www.sigma-genosys.com/peptide_design.asp (Accessed Dec. 16, 2004), 2 pages).*
Berendsen (H..J.C. Berendsen. A Glimpse of the Holy Grail? Science (1998) 282, pp. 642-643).*
Voet (D. Voet and J.G. Voet. Biochemistry, 2nd Edition. (1995), pp. 235-241).*
Robert T. Jensen, "Involvement of Cholecystokinin/Gastrin-Related Peptides and their Receptors in Clinical Gastrointestinal Disorders," Pharmacology & Toxicology, vol. 91, p. 333.*
Sporn et at, "Chemoprevention of Cancer," Carcinogenesis, vol. 21 (2000), 525-530.*
Gura, "Cancer Models: Systems for Identifying New Drugs Are Often Faulty," Science vol. 278 (1997), 1041-1042.*
Kwekkeboom, et al., "Cholecystokinm receptor imaging using an octapeptide DTPA-CCK analouge in patients with medullary thyroid carcinoma", European Journal of Nuclear Medicine, vol. 27, No. 9, Sep. 2000, pp. 1312-1317.*
PCT International Search Report for PCT/EP02/05562 dated Mar. 31, 2003.
PCT International Preliminary Examination Report for PCT/EP02/05562 dated Jul. 4, 2003.
Romani, S., et al.; "Synthesis of the trypsin fragment 10-25/75-88 of mouse nerve growth factor", Int. J. Peptide Protein Res. 29, 1987, 101-117.
Schaffhausen, et al.; "Antibody to the Nonapeptide Glu-Glu-Glu-Gly-Tyr-Met-Pro-Met-Glu Is specific for Polyoma Middle T Antigen and Inhibits in Vitro Kinase Activity", The Journal of Biological Chemistry, vol. 257, No. 21, Nov. 10, 1982, pp. 12467-12470.
Kwekkeboom, et al.; "Cholecystokinin receptor imaging using an octapeptide DTPA-CCK analouge in patients with medullary thyroid carcinoma", European Journal of Nuclear Medicine, vol. 27, No. 9, Sep. 2000, pp. 1312-1317.
Behr, et al.; "Targeting of cholecystokinin-B/gastrin receptors in vivo: preclinical and initial clinical evaluation of the diagnostic and therapeutic potential of radiolabelled gastrin", European Journal of Nuclear Medicine, vol. 25, No. 4, Apr. 1998, pp. 424-430.

* cited by examiner

*Primary Examiner*—Anish Gupta
*Assistant Examiner*—Thomas S. Heard
(74) *Attorney, Agent, or Firm*—Kramer Levin Naftalis & Frankel LLP

(57) ABSTRACT

This patent application describes the preparation of cyclic and branched peptides of general formula (I) and their conjugated derivatives labelled with a paramagnetic or radioactive metal. The compounds of the present invention are used as diagnostic agents to identify and locate primary tumours and their metastases which over-express type A and/or B cholecystokinin receptors, and as therapeutic agents and cholecystokinin agonists or antagonists.

18 Claims, 3 Drawing Sheets

Figure 1:
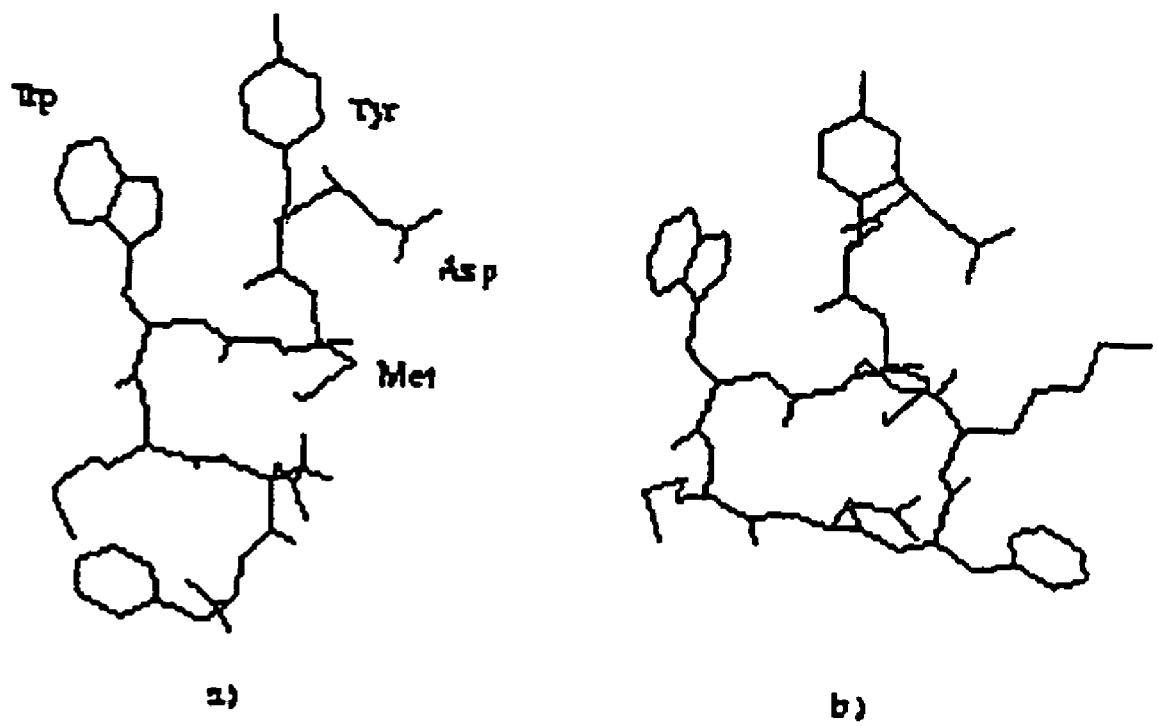

PREPARATION AND USE OF CYCLIC AND BRANCHED PEPTIDES AND THEIR LABELLED DERIVATIVES AS THERAPEUTIC AGENTS, CHOLECYSTOKININ AGONISTS OR ANTAGONISTS, AND DIAGNOSTIC AGENTS TO IDENTIFY AND LOCATE TUMOURS

The present invention relates to cyclic and branched peptides of general formula (I) and their derivatives conjugated with a spacer molecule Y and a chelating agent C, labelled with a paramagnetic or radioactive metal.

The compounds of the invention are used as diagnostic agents to identify and locate primary human tumours and their metastases which over-express type A and/or type B cholecystokinin receptors, and as therapeutic agents and cholecystokinin agonists or antagonists.

Cholecystokinins (CCKs) are a family of peptide molecules whose biological action is performed as a hormone and a neurotransmitter. All the CCKs originate from a process of fragmentation which takes place on a pre-hormone consisting of 115 amino acid residues, followed by a post-translational process of alpha-amidation of the C-terminal phenylalanine residue and sometimes, sulphation of the tyrosine residue contained in the C-terminal portion. The cholecystokinins therefore exist in various molecular forms; the most important ones have a sequence of 58, 39, 33 or 8 amino acid residues, and they all have the same C-terminal sequence of 8 amino acid residues:

Asp-Tyr-Met-Gly-Trp-Met-Asp-Phe-amide.

The form containing this sequence only is known as CCK8.

The biological activity of cholecystokinin depends on the type of receptor with which it interacts. Two types of receptor are known: type A and type B. In non-pathological situations, type A receptor is present in the tissues of peripheral organs such as the stomach, gall bladder, intestine and pancreas. The most important physiological actions due to the interaction of the CCK peptide hormone with type A receptor are contraction of the gall bladder, secretion of pancreatic enzymes, regulation of secretion, and absorption into the gastrointestinal tract. Type B receptor is mainly present in the central nervous system, where the interaction with cholecystokinin causes analgesia, satiety and anxiety, and regulates the release of dopamine.

Both the cholecystokinin receptors belong to the class of G-Protein Coupled Receptors (GPCRs), membrane receptors with seven transmembrane helixes joined by intra- and extra-cellular loops with an extracellular N-terminal arm and an intracellular C-terminal part. Both receptors have high affinities for the various forms of cholecystokinin; however, type A receptor has a greater affinity for the sulphated forms of cholecystokinin, namely the ones which contain a sulphuric group on the Tyr 27 residue, while type B receptor has a high affinity for the various forms of non-sulphated cholecystokinin and for gastrin. A series of peptide and non-peptide cholecystokinin-analog molecules with agonist or antagonist activity for type A and type B receptors are known (P. De Tullio, Current Medicinal Chemistry, 6, 433, 1999; F. Noble, Progress in Neurobiology, 58, 349, 1999). No pharmacological application has been found for any of the known molecules due to their low bioavailability and low solubility or high enzymatic degradation.

Cholecystokinin receptors have recently been identified in primary human tumours and metastases (J. C. Reubi, Cancer Research, 57, 1377, 1997, WO9731657). The use of functional peptides labelled with radioactive metals such as $^{125}$I (Biochemical Journal, 89, 114-123, 1963), $^{111}$In or $^{115}$In, used in nuclear medicine to visualise human tumours, is described in particular in that article and in the patent cited by J. C. Reubi.

Type A receptor in particular is over-expressed in pancreatic and oesophageal tumours, while type B receptor has been found to be over-expressed in small lung cell tumour, tumours of the colon and gastrointestinal tract, medullary thyroid tumours, astrocytomas and ovarian stromal tumours.

Some peptides deriving from cholecystokinin modified with chelating agents of radioactive or paramagnetic metals have been studied in clinical trials. In particular, CCK8 derivatives containing the chelating agents DTPA or DOTA which complex radioactive metals like $^{111}$In and $^{90}$Y, and their application to identify and treat tumours that over-express type B cholecystokinin receptor, have been reported (M. De Jong, Journal of Nuclear Medicine, 40, 2082, 1999).

The NMR structure of the complex between the non-sulphated peptide CCK8 and the N-terminal part of type A cholecystokinin receptor, responsible for the interaction with the peptide hormone, was recently published (M. Pellegrini, Biochemistry, 38, 14775, 1999). The N-terminal part of the receptor (receptor fragment) consists of 47 amino acids, and represents the extracellular N-terminal arm and the first part of transmembrane helix 1 of the type A receptor. This fragment does not contain the residue of Arg 197, present on the transmembrane loop, which is responsible for the interaction with the sulphuric group of Tyr 27 of CCK 8, with the result that peptide CCK8 is not used in the sulphated form (V. Gigoux, Protein Science, 8, 2347, 1999). In addition to the detailed structural information indicated in the NMR study, a recent study performed by observing the variations in fluorescence of the tryptophan residues present on the receptor fragment and the peptide confirmed the binding (R. Ragone, Biopolymers, 47-53, 56, 2001, publication pending), and enabled the affinity constant between non-sulphated CCK8 and the receptor fragment to be determined.

DESCRIPTION OF THE INVENTION

The compounds object of the present invention are cyclic peptides of general formula (I):

(I)

wherein:

Xaa, independently of each other, is any amino acid;

Xbb is an alpha or beta amino acid containing at least three functional groups selected from the group consisting of:

—COOH, —NH$_2$, —SH and —OH, n is between 0 and 15, and m is between 2 and 12.

Xbb is preferably selected from the group consisting of:

Lys, Asp, Glu, Cys, Orn, Dap, Dab, Gaba, epsilon-Aca and delta-Ava.

The invention also relates to compounds of formula (I) which are labelled, either with the use of a chelating group or directly, with radioactive or paramagnetic metals or radioactive halogens and the salts thereof with physiologically acceptable organic or inorganic bases or with anions of physiologically acceptable organic or inorganic acids.

At least one of Xaa amino acids will preferably be a residue of methionine (Met), tyrosine (Tyr) or tyrosine-m-sulphonate (SO3H-Tyr).

If the sulphate group is present on the tyrosine residue (Tyr or SO3H-Tyr), interaction with type A cholecystokinin receptor will be aided; conversely, a non-sulphated tyrosine residue (Tyr or SO3H-Tyr) sometimes may promote the interaction with type B cholecystokinin receptor.

The term "any amino acid" used above refers to the L and D isomers of the natural amino acids and "non-protein" amino acids commonly used in peptide chemistry to prepare synthetic analogs of natural peptides, such as alpha amino acids substituted and not substituted at the alpha and beta positions of the L and D configurations, and unsaturated alpha/beta amino acids.

Examples of "non-proten" amino acids are norleucine, norvaline, alloisoleucine, allothreonine, homoarginine, thioproline, dehydroproline, hydroxyproline, pipecolic acid, azetidine acid, homoserine, cyclohexylglycine, alpha-amino-n-butyric acid, cyclohexylalanine, aminophenylbutyric acid, phenylalanine mono and di -substituted at the positions ortho, meta and para of the aromatic ring, O-alkylated derivatives of serine, threonine and tyrosine, S-alkylated cysteine, epsilon-alkylated lysine, delta-alkylated ornithine, aromatic amino acids, substituted at the positions meta or para of the ring such as phenylalanine-nitrate, -sulfate, -phosphate, -acetate, -carbonate, -methylsulfonate, -methylphosphonate, tyrosine-sulfate, -phosphate, -sulfonate, -phosphonate, para-amido-phenylalanine, C-alpha,alpha-di-alkylated, amino acids such as alpha,alpha-dimethylglycine (Aib), alpha-aminocyclopropane-carboxylic acid (Ac3c), alpha-aminocyclobutane-carboxylic acid (Ac4c), alpha-aminocyclopentanecarboxylic acid (Ac5c), alpha-aminocyclohexanecarboxylic acid (Ac6c), diethylglycine (Deg), dipropylglycine (Dpg), diphenylglycine (Dph). Examples of beta-amino acids are beta-alanine (beta-Ala), cis and trans 2,3-diaminopropionic acid (Dap).

Other non-protein amino acids are identified on the website http://CHEMLIBRARY.BRI.NRC.CA/.

Preferred compounds of formula (I) are those wherein:

a) m is an integer between 4 and 8, n is an integer between 3 and 5, and the Xaa amino acids include at least one methionine residue and one tyrosine residue in the sulphonated or non-sulphonated form;

b) m is an integer between 4 and 8, n is an integer between 3 and 5, and the Xaa amino acids include at least one methionine residue, one tyrosine residue in the sulphonated or non-sulphonated form, and one lysine residue;

c) m is an integer between 4 and 8, n is an integer between 3 and 5, and the Xaa amino acids include at least one methionine residue, one tyrosine residue in the sulphonated or non-sulphonated form, one lysine residue or one amino acid selected from ornithine, aspartic acid and glutamic acid.

Particularly preferred compounds are peptides of general formula (II):

wherein
m is 4;
n is an integer between 3 and 5;
Xaa1 and/or Xaa2 may be absent;
Xaa3 is Asp or Glu;
Xaa4 is Tyr or SO3H-Tyr;
Xaa10 is Phe or an amino acid selected from Leu, Ile, Val, Ala, Trp, Gly and Pro.

Even more particularly preferred are peptides of formula (III-VIII):

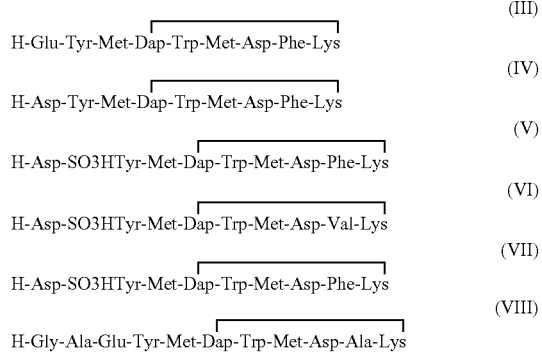

The compounds of the invention are synthetised by known techniques such as solid-phase peptide synthesis, peptide synthesis in solution, organic chemistry synthesis methods, or any combination of those techniques. Synthesis methods based on appropriate combinations of solid-phase techniques and conventional methods in solution, which involve low production costs, especially on an industrial scale, will preferably be used. These methods involve solid-phase synthesis of the peptide, including branching with the use of protected amino acids with orthogonal functions, possibly solid-phase conjugation of the macrocycle, cleavage of the protective peptide from the resin, solution cyclisation in diluted concentrations, and purification of the compound.

The compounds prepared according to general formula (I) can be labelled with radioactive or paramagnetic metals or radioactive halogens, either directly or using a chelating group.

A further object of the present invention are the compounds of general formula (IX):

wherein
A is a peptide of general formula (I);
z is an integer between 0 and 5;
Y is a spacer chain respectively bonded to one of the functionalities present on the side chains of the individual amino acids present in peptide A, or to an N-terminal (—NH₂) group or a C-terminal (—CO₂H) group of A, and to C; when z is an integer between 2 and 5, units Y may be the same or different from each other;

C is a chelating agent, bonded covalently to spacer chain Y or directly to peptide A, or to more than one amino acid units of peptide A, which is able to complex a paramagnetic metal or a radioisotopes.

Y is preferably a group of formula:

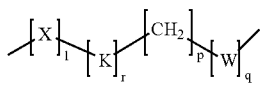

wherein r, l, and q are each independently 0 or 1, and p can vary between 0 and 10, provided that at least one of l, r and q is other than zero;

X is an O atom, or a —NR group wherein R is an H atom or an alkyl group ($C_1$-$C_5$);

K is a benzene nucleus, substituted or non-substituted, or a —$CHR_1$ group, wherein $R_1$ is a hydrogen atom or a —COOH or —$SO_3H$ group;

W is a —CO— or —CS— group.

Preferred compounds of formula (IX) are those in which the spacer chains Y have the following formulae (X), (XI) and (XII).

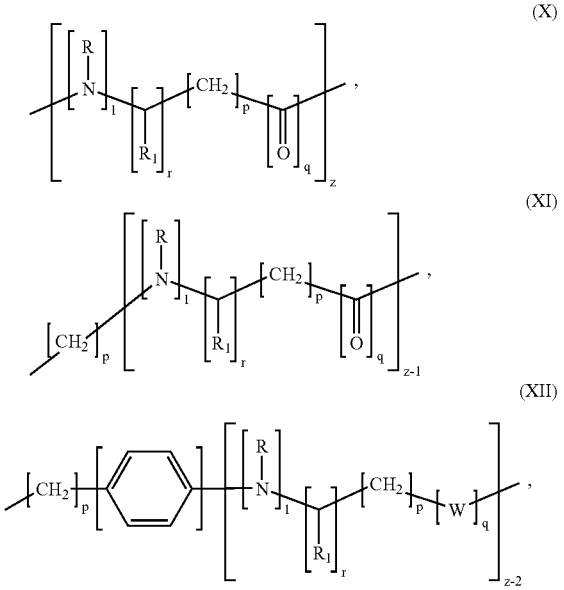

Particularly preferred are the compounds (IX) in which Y represents one of the following groups:

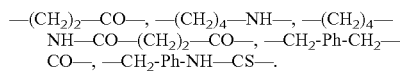

C preferably represents a chelating group selected from the group consisting of:

a residue of a polyaminopolycarboxylic acid and the derivatives thereof, in particular selected from diethylenetriaminopentaacetic acid (DTPA), 1,4,7,10-tetraazacyclododecane-1,4,7,10-tetraacetic acid (DOTA), 1,4,7,10-tetraazacyclododecane-1,4,7-triacetic acid (DO3A), [10-(2-hydroxypropyl)-1,4,7,10-tetraazacyclododecane-1,4,7-triacetic acid (HPDO3A), 4-carboxy-5,8,11-tris(carboxymethyl)-1-phenyl-2-oxa-5,8,11-triazatridecan-13-oic acid (BOPTA), N-[2-[bis(carboxymethyl)amino]-3-(4-ethoxyphenyl)propyl]-N-[2-[bis(carboxymethyl)amino]ethyl]glycine (EOB-DTPA), N,N-bis[2-[(carboxymethyl)[(methylcarbamoyl)methyl]amino]ethyl]-glycine (DTPA-BMA), 2-methyl-1,4,7,10-tetraazacyclododecane-1,4,7,10-tetraacetic acid (MCTA), (α,α',α",α'")-tetramethyl-1,4,7,10-tetraazacyclododecane-1,4,7,10-tetracetic acid (DOTMA); or is the residue of a polyaminophosphate acid ligand or derivatives thereof, in particular N,N'-bis-(pyridoxal-5-phosphate)ethylenediamine-N,N'-diacetic acid (DPDP) and ethylenedinitrilotetrakis(methylphosphonic) acid (EDTP); or is the residue of a polyaminophosphonic acid ligand and derivatives thereof, or polyaminophosphinic acid and derivatives thereof, in particular 1,4,7,10-tetraazacyclododecane-1,4,7,10-tetrakis[methylene(methylphosphonic)]acid and 1,4,7,10-tetraazacyclododecane-1,4,7,10-tetrakis[methylene-(methylphosphinic)]acid; or is the residue of macrocyclic chelants such as texaphrines, porphyrins, phthalocyanines; or is N,N-bis[2-[bis(carboxymethyl)amino]ethyl]L-glutamic acid (DTPA-GLU) or DTPA conjugated with Lys (DTPA-Lys).

The cyclic and/or branched peptide A can be linked to the chelating group C, directly with a covalent bond between two functional groups of A and C, or by the spacer chain Y and this can be obtained, for example, with the acid groups of the ligand, or by a suitable reactive group present in the starting ligand, for example an amino group, or a functional group present on a phenyl, etc.

Particularly preferred reactive groups present on C or Y, are selected from the group consisting of —$CO_2H$, —$NH_2$, —NCS, —$NHCSNHNH_2$, —$NHCSNH(CH_2)_2NH_2$, —NCO, —$NHNH_2$, —$NHCONHNH_2$, —CHO.

Particularly preferred are the compounds of formula (IX) in which C is a residue of the ligand DTPA, DO3A or DOTA.

Further examples of chelating groups C, which can be used in particular as chelating agents for radionuclides (such as Tc, Re, Cu, Ga) are amino/amide thiol derivatives that can be represented by the general formula (XIII), wherein J is included within the range 0÷2 and has generally unitary value.

(N amino/amido)$_{4-j}$(S thiol derivative)$_j$     (XIII)

Preferred chelating groups of formula (XIII) include $N_4$ aminopropylene oximes, diaminedioximes, hydrazines, $N_3S$ triamide monothiols, $N_2S_2$ diamido dithiols, diamine dithiols, monoamide monoaminedithiols and monoamine monoamidedithiols.

A large number of applications of the chelating compounds of formula (XIII), labelled with Technetium or Rhenium are known in literature.

Preferred chelating agents C of metal ions and in particular of rhenium or technetium of formula (XIV a), (XIV b), (XIV c) and (XV) are disclosed in EP 629,617, EP 544,412, U.S. Pat. No. 5,663,307 and U.S. Pat. No. 5,651,954, respectively, the content of which is incorporated herein by reference, in particular as far as the definition of the groups Q, R, R*, G1, G2 and R1 are concerned.

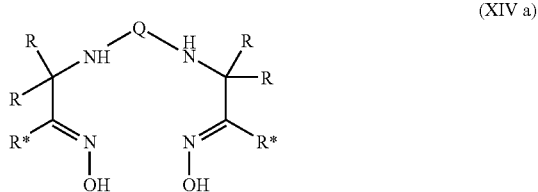

-continued

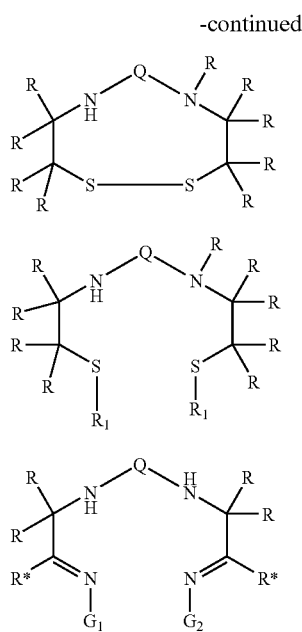

(XIVb)

(XIVc)

(XV)

A further example of a compound which can be used as a chelating group C of formula (XIII), is dimethylglycine-L-serine-L-cysteinylglycinamide (XVI), which has proved to be of considerable interest and suitable for use as a bifunctionalised ligand for conjugation to peptides and proteins and for complexing of the radionuclide $^{99m}$Tc or $^{188}$Re. Other derivatives which can be used as chelating agents C are disclosed in WO9933863, the content of which is incorporated herein by reference.

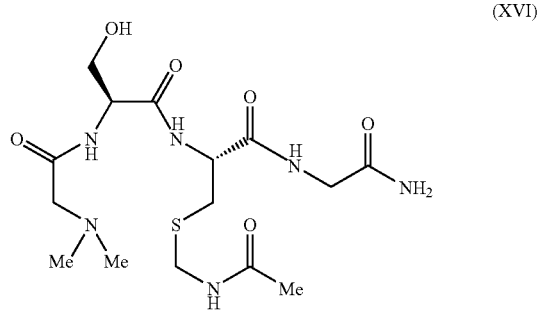

(XVI)

The functionalisation of the chelating groups of formula (XIII) enables them to be used as conjugates bonded with covalent bonds for a wide range of biologically active molecules.

In particular, in the preparation of compounds of formula (IX) used in nuclear medicine diagnostics, chelating compounds C are selected in such a way as to obtain corresponding stable complexes with radioisotopes that emit gamma, beta or positron radiation, using for example the radioisotopes of Tc, Re, Tl, In, Cu, Ga, Rb or Y.

The use of $^{99m}$Tc in nuclear medicine diagnostics is known, and it offers a number of advantages which make it one of the most commonly used radio nuclides. Its 6-hour half-life is short enough for the administration of a dose of radiation that provides high-quality images without risk to the patient's health.

Numerous techniques have also been developed which enable Tc to be bonded to various molecules with biological activity, such as antibodies, proteins and peptides.

The binding between the molecule and the radionuclide is usually obtained by one of the following methods:

a) direct binding of the radionuclide to the molecule concerned, which is effected, for example, with the use of a reducing agent that reduces the disulphide bridges of a peptide or a protein to two hydrosulphide groups, which directly bind Tc(V);

b) the use of a chelating agent C of the type described above, generally bifunctionalised, in which one functionality is used for the direct binding to the peptide (or to the compound, in accordance with general formula Y, conjugated to A) and the other is used for complexing with the radionuclide, which is performed before or after binding with the biologically active molecule, as the case may be (preformed-chelate or final-step-labelling method).

The radioactive complex is prepared by methods described in the literature, such as by reaction of the functionalised chelating compound with a salt, in which Tc-99m pertechnetate is preferably used, in the presence of a suitable reducing agent.

The reducing agents used include those reported in the literature, such as dithionite, ferrous and stannous ions (e.g. tartrate, chloride and fluoride), or other solid-state reducing agents.

This type of complex is usually prepared with an inactive diagnostic kit, previously prepared under aseptic conditions, which contains a predefined amount of the compound conjugated with the chelating agent in the form of a freeze-dried powder, and of the reducing agent, both formulated in the presence of suitable stabilising agents, surfactants and/or buffers which can be used to prepare the pharmaceutical bulk product.

The solution containing the chelating agent is usually suitably formulated and subsequently distributed into vials which are freeze-dried and closed under nitrogen atmosphere to ensure that the properties of the reducing agent (e.g. stannous chloride) present in the composition are maintained.

The inactive kits thus prepared are subsequently reconstituted, for example with a sodium pertechnetate solution, to form the corresponding complexes with $^{99m}$Tc, which are used in radiological diagnostics for functional and morphological examinations of organs of the human body, and in particular, for the compounds of the invention, which are used for imaging of tumors that over-express cholecystokinin receptors.

The use of radioactive rhenium isotopes as an alternative to technetium isotopes has been proposed by Wong et al. (Wong, Inorganic Chemistry, vol. 36, 5799-5808, 1997), especially in the coordination state (V), and isotopes $^{186}$Re and $^{188}$Re have proved to be of particular interest in nuclear medicine, having a large number of applications in radiopharmaceutical therapy.

Another class of chelating compounds C, which are suitable for conjugation with the compounds of the invention and can be used not only as chelators of paramagnetic metals (MRI) but also of radioactive metals (radiotherapy and radiodiagnostics), consists of polyazamacrocycles of formula (XVII). These chelating compounds contain at least one amine, thiol, carboxyl or carboxyl derivative group or a thiocarboxylate, present as free functionality and suitable for use in the conjugation reaction to spacer chain Y or peptide A, and according to the general formula (IX).

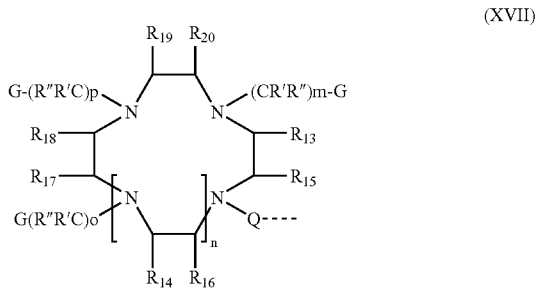

(XVII)

For a complete description of the compounds of formula (XVII), see U.S. Pat. No. 6,093,382, which is incorporated herein by reference.

Compounds (I) and (IX) can form chelates with the bi-trivalent ions of the metal elements having atomic number ranging between 20 and 31, 39, 42, 43, 44, 49, and between 57 and 83, with radioactive isotopes of metals or halogens ($^{123}$I, $^{125}$I, $^{131}$I, $^{75}$Br, $^{76}$Br, $^{74}$Br, $^{77}$Br and $^{82}$Br) or paramagnetic metals ($^{99m}$Tc, $^{203}$Pb, $^{67}$Ga, $^{68}$Ga, $^{72}$As, $^{111}$In, $^{113}$In, $^{90}$Yt, $^{97}$Ru, $^{82m}$Rb, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{188}$Re, $^{186}$Re, $^{161}$Tb and $^{51}$Cr), possibly in the form of salts with physiologically compatible bases or acids.

Particularly preferred are the complexes with $Fe(^{2+})$, $Fe(^{3+})$, $Cu(^{2+})$, $Cr(^{3+})$, $Gd(^{3+})$, $Eu(^{3+})$, $Dy(^{3+})$, $La(^{2+})$, $Yb(^{3+})$ or $Mn(^{2+})$ or with radioisotopes such as $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{90}$Y, $^{149}$Pm, $^{177}$Lu, $^{47}$Sc, $^{142}$Pr, $^{159}$Gd and $^{212}$Bi.

Preferred cations of inorganic bases suitable for salifying the complexes of the invention comprise, in particular, alkali or alkaline-earth metal ions such as potassium, sodium, calcium, magnesium.

Preferred cations of organic bases comprise those of primary, secondary and tertiary amines, such as ethanolamine, diethanolamine, morpholine, glucamine, N-methylglucamine, N,N-dimethylglucamine.

Preferred anions of inorganic acids comprise, in particular, the ions of halo acids such as chlorides, bromides, iodides or other ions such as sulfate.

Preferred anions of organic acids comprise those of acids conventionally used in pharmaceutical technique for the salification of basic substances, such as acetate, succinate, citrate, fumarate, maleate, oxalate.

Preferred cations and anions of amino acids comprise, for example, those of taurine, glycine, lysine, arginine or ornithine or of the aspartic and glutamic acids.

Compounds (I) and (IX) are also useful as cholecystokinin agonists or antagonists and, after labelling, either with the use of a chelating group or directly with radioactive or paramagnetic metals or radioactive halogens, as therapeutic and diagnostic agents to identify and locate primary human tumors and their metastases which over-express type A and/or B cholecystokinin receptors. Binding to the receptor may be followed by a process of internalisation in the cells.

In particular, compounds of formula (IX), labelled with paramagnetic metals, have proved to be useful contrast media for magnetic resonance, especially for imaging of animal tumour cells which over-express type A and/or type B cholecystokinin receptors.

Compounds (I) possess particular characteristics which make them suitable for the purposes described above, in which:

a) they take on a structure in solution such that they can interact specifically with type A and/or type B cholecystokinin receptors, and have at least comparable affinity for CCK8;

b) as a result of the presence of the cycle, they are particularly stable to enzymatic degradation under physiological conditions;

c) they take on a conformation such that the presence of a chelating substituent does not interfere with binding to the receptor.

Compounds of formula (IX) can be prepared by conventional synthetic methods. In particular, a compound of formula (IX) can be obtained with convergent synthesis, which involves:

1) synthesis of a functionalised ligand, namely a ligand able to coordinate a paramagnetic metal ion or the isotope of a radioactive metal, which can also bind stably to the peptide, either directly or through a suitable functional group;
2) synthesis of the peptide;
3) coupling reaction between the two different synthons, including with the use of spacer unit Y;
4) cleavage of any protective groups;
5) complexing with a paramagnetic or radioactive metal ion.

The two synthons are conjugated by various known coupling methods widely used in synthesis (see, for example, Brinkley, M., Bioconjugate Chem. 1992, 3, 2), which involve for example the formation of an amide, a thiourea or an ester.

Radioactive halogens used in therapy and diagnosis are known. For example, $^{123}$I is known for its use in imaging, while $^{131}$I can be used not only for imaging, but preferably in therapy. The bromine radionuclides $^{75}$Br and $^{76}$Br are used for diagnosis, while $^{77}$Br is used in radiotherapy. $^{18}$F and $^{211}$At are used in diagnosis and radiotherapy.

If the radionuclide is an isotope of a radioactive halogen, it can be bonded directly to peptide (I) by reacting with a Trp or Tyr residue.

The methods of labelling with iodine isotopes include not only direct iodination with oxidative methods, but also the nucleophilic substitution reaction and the isotope exchange reaction. The choice of labelling method in this case depends on the structure of the precursor, the problems associated with the purification techniques, and the cost-effectiveness of the process used.

An example of an indirect labelling method with radioactive halogens which can be used with compounds of formula (I) is described in U.S. Pat. No. 5,290,937, incorporated herein by reference, which enables radio-labelled proteins of formula (XVIII) to be obtained:

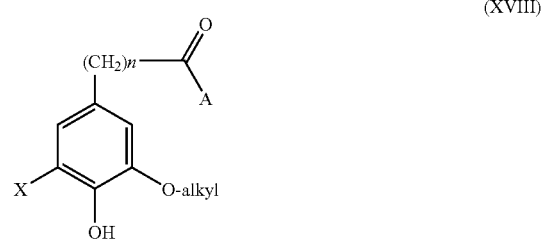

(XVIII)

wherein X is a radionuclide selected from $^{125}$I, $^{131}$I, $^{123}$I, $^{75}$Br, $^{76}$Br and $^{77}$Br, and A has the meaning described above for compounds of formula (I).

The use of the corresponding compounds labelled with radioisotopes which emit gamma rays or alpha or beta particles enables a quantity of product sufficient to have a cytotoxic effect to be conveyed to the site in question. The radioactive decay of the isotope is generated at the tumour binding site, and determines the presence of a sufficient quantity of local ionising radiation to be toxic to the tumour cells.

The binding specificity for the cells that over-express cholecystokinin receptors enables these compounds to minimise the exposure of normal cells to the cytotoxic agents, thus providing an effective treatment with lower side effects.

In the case of compounds of formula (I) and (IX), both soluble and less soluble compounds are suitable for oral or parenteral administration.

Compounds for parental administration are preferably formulated as a sterile aqueous suspension or solution, the pH of which can range, for example, between 6.0 and 8.5.

These aqueous suspensions or solutions can be administered in concentrations ranging between 0.002 and 1.0 molar.

These formulations can be freeze-dried in the form of powders and reconstituted at the time of use. For gastrointestinal use or injection into body cavities, these agents can be formulated as a suspension or solution containing additives suitable to control their viscosity, for example.

For oral administration they can be formulated in accordance with preparation methods commonly used in pharmaceutical technology, possibly as a coated formulation, in order to provide additional protection against the acid pH of the stomach; this prevents release of the chelated metal ion, which particularly occurs at the pH values typical of the gastric juices.

Other excipients, such as sweeteners and/or flavourings, can also be added in accordance with known techniques.

Compounds of formula (I) and (IX), suitably formulated, are particularly useful for visualising pancreatic and oesophageal tumors and other tumors that over-express type A cholecystokinin receptors, and for tumors of the small cells of the lung, colon and gastrointestinal tract, medullary thyroid tumors, astrocytomas, ovarian stromal tumors and other tumors which over-express type B cholecystokinin receptors.

The experimental part describes the synthesis of the compound of formula (IV).

$$\text{H-Asp-Tyr-Met-Dap-Trp-Met-Asp-Phe-Lys} \quad (IV)$$

The compound of formula (IV) demonstrates a conformational behaviour similar to that of the NMR complex between peptide CCK8 and receptor CCK-A.

FIG. 1 shows:

a) the structure of peptide CCK8 taken up into the complex with N-terminal fragment 1-47 of the type A CCK receptor, as reported by M. Pellegrini in Biochemistry, 38, 14775, 1999, and b) the expected structure of the cyclic compound of formula (IV).

The structure of the complex between non-sulphated peptide CCK8 and the N-terminal part of the type A cholecystokinin receptor, responsible for interaction with the peptide hormone, is deposited in the Protein Data Bank (http://www.rcsb.org) with the code "pdb1D6G.ent". The N-terminal part of the receptor (receptor filament) consists of 47 amino acid residues, and represents the extracellular N-terminal arm and the first part of transmembrane helix 1 of the type A receptor.

The study of the structure of the complex (fragment 1-47 of type A CCK receptor and peptide CCK8), performed with NMR spectroscopy, and the subsequent binding study performed with fluorescence spectroscopy, were carried out with peptide CCK8 in the non-sulphated form.

List of Abbreviations

For the nomenclature and abbreviations of the amino acids, reference should be made to the recommendations of the IUPAC-IUB Joint Commission on Biochemical Nomenclature (Eur. J. Biochem. 1984, 138, p. 9); the amino acids are in the L configuration unless otherwise specified.

The other abbreviations used are:

Orn=ornithine, Nle, norleucine, Hyp=hydroxyproline, delta-Pro=dehydroproline, delta-Glu=alpha-beta-dehydroglutamic acid, alpha-Me-Glu=acid alpha-methyl-glutamic, Cha=cyclohexylalanine, aIle=alloisoleucine, Chg=cyclohexylglycine, Sar=sarcosine, Deg=diethylglycine, Dpg=dipropylglycine, Aib=alpha-aminoisobutyric acid, Dap=2,3 diaminopropionic acid, Dab=2,4 diaminobutyric acid, epsilon-Aca=epsilon-aminocaproic acid, delta-Ava=delta-aminovaleric acid, beta-Ala=beta-alanine, $Ac_3c$=alpha-aminocyclopropanecarboxylic acid, $Ac_4c$=alpha-aminocyclobutanecarboxylic acid, $Ac_5c$=alpha-aminocyclopentanecarboxylic acid, Ac6c=alpha-aminocyclohexanecarboxylic acid, alpha-$Ac_5c$=alpha-aminocyclopentanecarboxylic acid, alpha-$Ac_6c$=alpha-aminocyclohexane-carboxylic acid, $NO_2$-Phe=nitrophenylalanine, $SO_3H$-Phe=sulfonated phenylalanine, $PO_3H_2$-Phe=phosphonated phenylalanine, $PO_4H_2$-Phe=phenylalanine phosphate, $SO_4H$-Phe=phenylalanine sulfate, $SO_3H$-Tyr=tyrosine-m-sulfonated, $PO_3H_2$-Tyr,=tyrosine-m-phosphonated, Boc=tert-butoxycarbonyl, Fmoc=fluorenylmethoxycarbonyl, TFA=trifluoroacetic acid, DCM=dichloromethane, DIEA=diisopropylethylamine, DMF=dimethylformamide, Obzl=benzyl ether, EDT=ethanedithiol, TIS=triisopropylsilane, HATU=O-(7-azabenzotriazol-yl)-1,1,3,3-tetramethyluronim tetrafluroborate, PyBop=benzotriazole-1-yl-oxi-tris-pyrrolidinium-phosphonium-hexafluophosphate, Trt=trityl, Pmc=2,2,5,7,8-pentamethyl-chroman-6-sulfonyl, Mtt=4-methyl-trityl, Dde=1-(4,4-dimethyl-2,6-dioxo-cyclohexyldene)-ethyl, Opfp=pentafluorophenyl ester, tBu=tert-butyl ether, OtBu=tert-butyl ester, Ac=acetyl, HPLC=high pressure liquid chromatography.

The following examples further illustrate the invention.

EXAMPLE 1

Synthesis of the cyclic peptide of formula (IV):

$$\text{H-Asp-Tyr-Met-Dap-Trp-Met-Asp-Phe-Lys} \quad (IV)$$

The peptide of formula (IV) contains the non-natural amino acid Dap (2,3-diaminopropionic acid), and this residue is used to form the cyclic peptide thanks to the formation of the amide bond between the C-terminal carboxyl group of the amino acid lysine and the amino group in position 3 of 2,3-diaminopropionic acid.

The peptide was synthesised with the solid-phase peptide synthesis strategy, using the Shimadzu automatic peptide synthesiser for batch synthesis. In particular, the method that uses the Fmoc group as alpha-amino function protective group was employed. The solid medium used for the synthesis was 2-chloro-trityl-chloride resin, which consists of a polystyrene medium with 2% divinylbenzene functionalised with the chloride group of 2-chloro-trityl; this resin allows the carboxyl C-terminal peptide, completely protected on the side chains of the amino acids, to be obtained by hydrolysis in weakly acid conditions.

A synthesis scale of 0.176 mmoles was used. This synthesis scale was obtained by using 400 mg of resin, which was previously partly functionalised with the first amino acid, Fmoc-Lys(Boc).OH, in accordance with the following procedure. A manual batch reactor was used, and the amino acid deficit (0.6 equivalents) with respect to the functional groups present on the resin (0.83 mmoles/g) was added in DCM; an equivalent amount of PyBop and 4 DIEA equivalents, with respect to the amount of amino acids used, were added. The number of mmoles of amino acid bound to the resin was estimated on one aliquot by evaluating the amount of the Fmoc group present on the amino group in the alpha position of the lysine residue and removed with a basic solution containing 20% by volume of piperidine in DMF, and measuring the absorbance of the chromophore effected in the UV region (lambda=290, $epsilon_{290}=5.10^3$). After this procedure, the degree of substitution of the 2-chloro-trityl-Lys(Boc)-Fmoc resin was 0.44 mmoles/g. Synthesis of the peptide was then completed by transferring the resin bonded to the first amino acid (Fmoc-Lys(Boc)-) into the reactor of the synthesiser, and programming the synthesis with the following procedure: surplus of individual amino acids 2.5 equivalents, activating PyBop 1 equivalent with respect to the amino acid, DIEA 1.5 equivalents with respect to the amino acid and PyBop, anhydrous DMF solvent, coupling time 60 minutes (single coupling). The amino acids used in sequence were as follows: Fmoc-Phe-OH, Fmoc-Asp (OtBu)—OH, Fmoc-Met-OH, Fmoc-Trp(Boc)—OH, Fmoc-Dap(Dde)—OH, Fmoc-Met-OH, Fmoc-Tyr(tBu)—OH and Boc-Asp(OtBu)—OH. When assembly of the peptide on the resin had terminated, the Dde protective group of the side chain of the Dap residue was removed by treating it with a 4% hydrazine solution in DMF. Two successive 10-minute treatments were used for this deprotection reaction. Next, the cleavage reaction of the peptide partly protected by the resin was performed; the resin was placed on a porous septum. and treated with an 0.5% solution (by volume) of TFA in dichloromethane for 3-5 minutes, the operation being repeated 10 times. The acid washing solution was collected in a flask containing 10% pyridine. After removing 90% of the starting solvent volume by evaporation at reduced pressure, the peptide was precipitated by addition of cold water and subsequently washed with water. After checking with Maldi mass spectroscopy for the presence of the peptide with all the protective groups except for the one on the Dap side chain (molecular weight 1691), the cyclisation reaction was performed. The C-terminal carboxyl group on the lysine residue formed an amide bond with the amino group in position 3 of 2,3-diaminopropionic acid. The reaction was carried out in DMF at a peptide concentration of $5.10^{-4}$M by adding the carboxyl function activator HATU in excess of 4 equivalents and the DIEA base to a pH of 8.5. The mixture was kept under stirring for 5 hours at 40° C. The solvent was then removed under reduced pressure, and the protective groups cleaved by the following procedure. The cyclic peptide was treated in a flask under stirring for 2 hours with a mixture of TFA containing EDT (2.5%), TIS (1%) and water (2.5%). The homogeneity of the crude product was checked by analytical HPLC; the crude product presented a main peak with a retention time of 16.7 minutes (column: reverse phase C18; eluents: water with 1% TFA and acetonitrile with 1% TFA; elution gradient: water percentage from 80% to 20% in 25 minutes). The product was purified by preparative HPLC, with the same separation method as used on an analytical scale. The purity of the product obtained exceeded 98%, as confirmed by analytical HPLC, with a yield exceeding 50% of the expected theoretical yield. The identity of the product was confirmed with Maldi mass spectroscopy, which showed a peak at the expected mass value: 1202.

EXAMPLE 2

Determination of binding between compounds of formula (IV) and fragment 1-47 of type A cholecystokinin receptor, $CCK_A$-R(1-47).

The binding between the compound prepared as described in example 1 and fragment 1-47 of type A cholecystokinin receptor was studied with fluorescence spectroscopy. Although the compound of formula (IV), as it has no sulphate functions on the tyrosine residue, should have greater affinity for type B cholecystokinin receptor, the experiment performed and the results obtained are entirely legitimate, because the receptor fragment used contains no residues (Arg 197) which are known to be responsible for interaction with the sulphate group. The study of the structure of the complex: fragment 1-47 of type A CCK receptor/ peptide CCK8 carried out with NMR spectroscopy, and the subsequent binding study performed with fluorescence spectroscopy, used peptide CCK8 in the non-sulphated form.

Fragment 1-47 of type A receptor, $CCK_A$-R(1-47), and the compound of formula (IV), both synthesised by solid-phase peptide synthesis methods, were used. Reference should be made to example 1 for the synthesis of compound (IV); for the synthesis of the receptor fragment, see R. Ragone, 47-53, 56, 2001, *Biopolymers*).

The interaction between receptor fragment CCKA-R(1-47) and compound (IV) was observed by monitoring the tryptophan fluorescence. The emission spectra were recorded at room temperature using a Jasco FP-750 spectrofluorimeter at the excitation wavelength of 296 nm to excite the tryptophan selectively. Small aliquots of a concentrated solution of compound (IV) dissolved in phosphate buffer at pH 7.2 were added to a fixed volume of a solution of $CCK_A$-R(1-47) dissolved in the same solvent, in the presence of a 10 mM solution of sodium dodecylsulphate micelles, used to mimic the cell membrane. The final spectra used in the calculations were corrected for dilution and the contributions of the individual molecules isolated.

Figure 2:
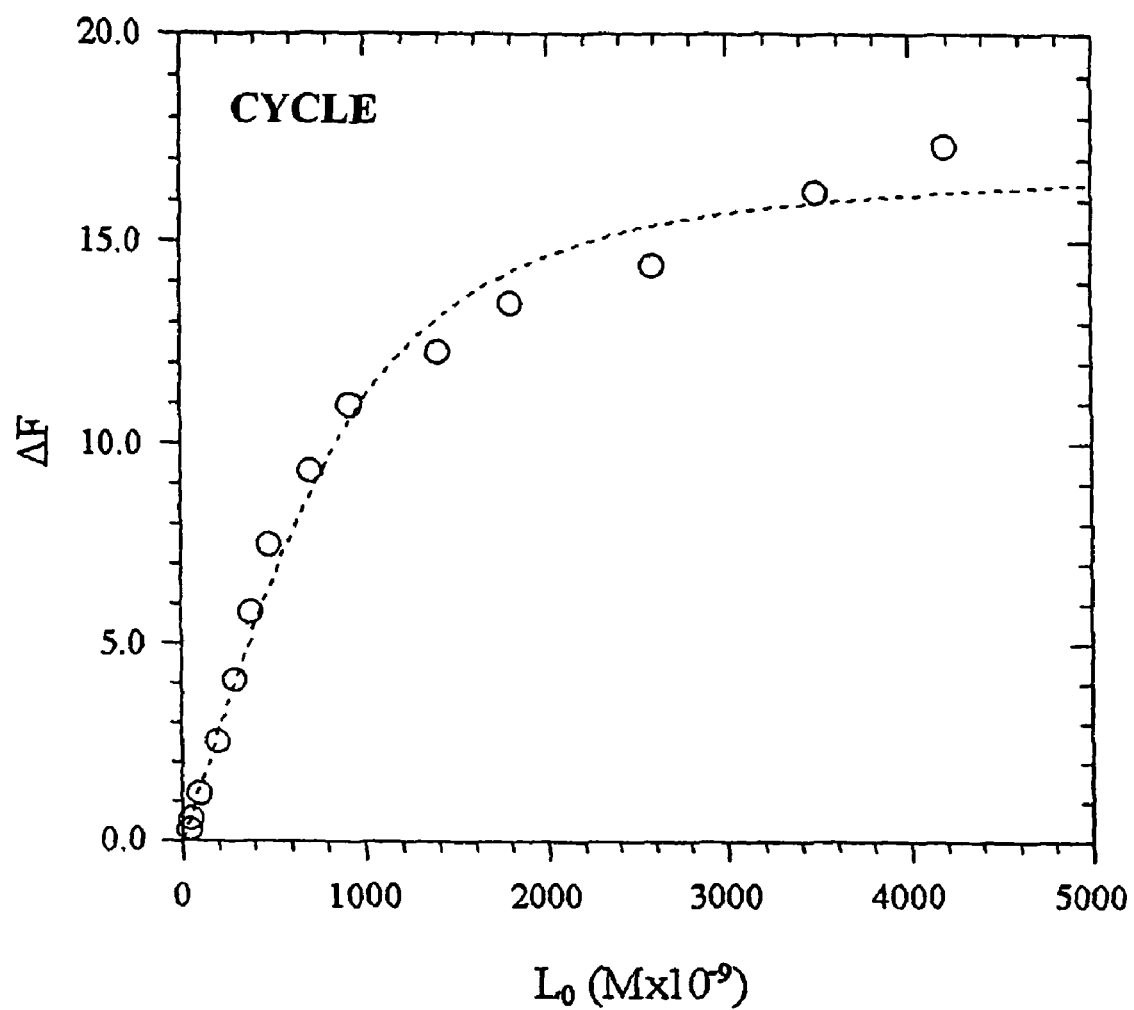

As shown in FIG. 2, evaluation of the graph gives the measurement of the binding of the peptide of formula (IV) to fragment 1-47 of type A cholecystokinin receptor, CCKA-R(1-47), wherein the receptor concentration is 2.6 µM in 10 mM of phosphate buffer, pH 7.2 (value measured by absorbance. at 280 nm), in the presence of a 10 mM solution of SDS micelles. Increasing quantities of compound of formula (IV) were added from a concentrated master solution containing 10 mM SDS micelles. The fluorescence was measured at 335 nm, and the binding curve resulting from the experiment agrees with a value of $K_d$=255 nM.

As will be seen in FIG. 2, which exemplifies a typical saturation curve, the fluorescence signal is gradually quenched as a result of the binding. The experiments were performed at various receptor concentrations, and fluorescence quenching was always observed. The same titration curve is found for any given experiment, regardless of the emission wavelength chosen to perform the calculations. To distinguish the modifications in fluorescence caused by the binding, the contributions to fluorescence of the receptor and peptide isolated were subtracted, and a small variation in fluorescence compared with the value measured was obtained. Although this involves a large statistical variation, it does not prevent correct evaluation of the quenching of the fluorescence. The fitting procedures used enabled us to estimate a value of $K_d$ in the 50-200 nM range, with a mean of 120 nM (standard deviation ±27 nM). This value is in the same submicromolar affinity range as found for non-sulphated linear binding of CCK8 to fragment 1-47 of type A receptor or the entire type B receptor.

EXAMPLE 3

Evaluation of the biological activity of the peptide of formula (IV).

Biological tests have been carried out to confirm the activity of the cyclic compound of formula (IV), using neurone cells which express type A cholecystokinin receptor. The activity of the compound of formula (IV) was compared with peptide CCK8 in the non-sulphated form on the tyrosine residue. Both these compounds should show a lower level of activity than the corresponding analogs containing the sulphate group on the tyrosine residue. The biological activity tests involved the use of myenteric neurones as receptor-expressing cells, and the use of a confocal microscope with a suitable software package to measure peptide activity. The tests were based on the following assumptions:

1) myenteric neurones (of the intestinal wall) normally express type A CCK receptor
2) binding between CCK and the receptor induces excitation of the cell (change in membrane potential), which can be recorded with electrophysiology studies
3) the cell excitation is coupled to the passage of calcium from the outside to the inside of the cell through specific membrane channels
4) if the calcium is rendered fluorescent (using calcium chelators which modify the emission wavelength if they are excited at a particular wavelength), the increased concentration of the intracellular calcium in response to a stimulus can be recorded
5) confocal laser microscopy with the aid of specific software therefore enables these phenomena to be recorded, and the fluorescence to be converted into the intracellular calcium concentration.

When the neurones were exposed to non-sulphated peptide CCK8 and to the cyclic analog described in example 1 (perfusion for 60 seconds), it was found that both substances induce an increase in the intracellular calcium concentration.

Figure 3:
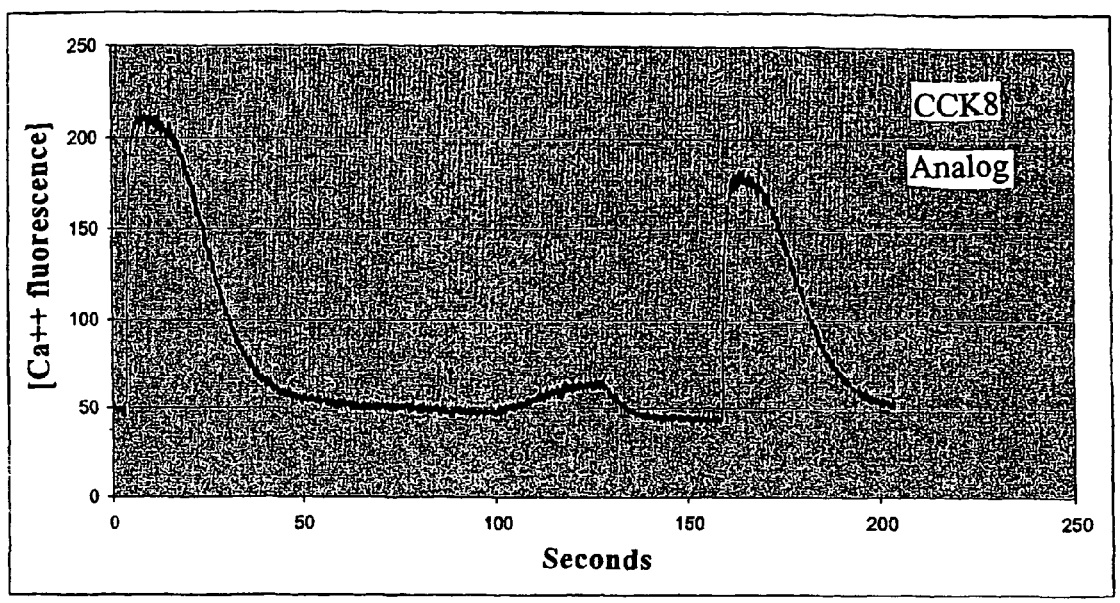

The test method is shown in FIG. 3. The graph, which shows two distinct curves, relates to the same cell at two different times: before it was infused with non-sulphated peptide CCK8 and after washout (approx. 5 mins.) with the cyclic peptide of formula (IV) described in example 1. The y-axis shows the fluorescence units, and the x-axis the perfusion time (in seconds). The graph shows a first maximum peak (excitation after perfusion with 75 mM $K^+$), which is the stimulus used to identify the neurones functionally, then the response to the CCK8 peptides and the cyclic peptide of formula (IV), and finally 75 mM $K^+$ again to confirm cell viability.

Although the experiment does not evaluate the potency of action of the two molecules examined, the result indicates that the synthesised analog is able to bind to the specific receptor and induce a cell response.

EXAMPLE 4

Preparation of the functionalised cyclic peptide of formula (XIX).

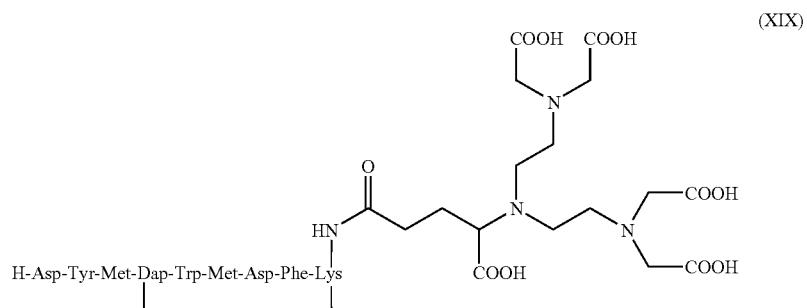

The peptide component of compound (XIX) is the same as described in example 1, and the side chain of the lysine residue present in the peptide part of the compound of formula (IV), namely N,N-bis[2-[bis(carboxymethyl)amino]ethyl]L-glutamic acid (DTPA-GLU), is also used to bind the chelating agent covalently.

The compound of formula (XIX) was synthesised similarly to compound (IV), using the solid-phase peptide synthesis strategy and employing synthesis procedures in manual reactors as well as the Shimadzu automatic peptide synthesiser for batch synthesis. In particular, the method that uses the Fmoc group as protective group of the alpha-amino function was employed. The solid medium used for the synthesis was 2-chloro-trityl-chloride resin, which consists of a polystyrene medium with 2% divinylbenzene functionalised with the chloride group of 2-chloro-trityl; this resin allows the carboxyl C-terminal peptide, completely protected on the side chains of the amino acids, to be obtained by hydrolysis in weakly acid conditions.

A synthesis scale of 0.180 mmoles was used. This synthesis scale was obtained by using 400 mg of resin, which was previously partly functionalised with the first amino acid, Dde-Lys(Fmoc)—OH, in accordance with the following procedure. A manual batch reactor was used, and the amino acid deficit (0.8 equivalents) with respect to the functional groups present on the resin (1.0.8 mmoles/g) was added in DCM; an equivalent amount of PyBop and 4 DIEA equivalents, with respect to the amount of amino acids used, were added. The number of mmoles of amino acid bound to the resin was estimated on one aliquot by evaluating the amount of the Fmoc group present on the amino group in the epsilon position of the lysine residue and removed with a basic solution containing 20% by volume of piperidine in DMF, and measuring the absorbance of the chromophore effected in the UV region (lambda=290, epsilon$_{290}$=5.10$^3$). After this procedure, the degree of substitution of the 2-chloro-trityl-Lys(Boc)-Fmoc resin was 0.44 mmoles/g. The Fmoc protective group was then cleaved from the amino function in the epsilon position of the Lys residue by treating it with a 20% solution of piperidine in DMF. Two successive 7-minute treatments were used for the deprotection reaction. At a later stage we performed the condensation reaction of the chelating agent DTPA-GLU, protected on five of its six carboxyl functions with terbutyl groups, through its single free carboxyl group, with the amino group in the epsilon position of the Lys residue bonded to the resin. The reaction was performed using HATU as activator, with a DTPA-GLU surplus of 2.5 equivalents, using the DIEA base to stabilise the pH at 8.5. The Kaiser test was performed to confirm that the coupling reaction was complete. The Dde protective group present on the amino function in the alpha position of the Lys residue was then cleaved by treating it with a 4% solution of hydrazine in DMF. Two successive 10-minute treatments were used for this deprotection reaction. This made it possible to perform the subsequent coupling reaction of the amino acid Fmoc-Phe-OH, again with a manual system, under the same reaction conditions as described for the chelating agent DTPA-GLU. The Kaiser test again confirmed that the coupling reaction was complete.

Synthesis of the peptide was then completed by transferring the Lys(Glu-DTPA)-Phe-Fmoc resin to the reactor of the automatic synthesiser and programming synthesis with the following procedure: surplus of the individual amino acids 2.5 equivalents, PyBop activator 1 equivalent with respect to the amino acid, DIEA 1.5 equivalents with respect to the amino acid and PyBop, solvent anhydrous DMF, coupling time 60 minutes (single coupling). The amino acids used in sequence were Fmoc-Asp(OtBu)-OH, Fmoc-Met-OH, Fmoc-Trp(Boc)-OH, Fmoc-Dap(Dde)-OH, Fmoc-Met-OH and Fmoc-Tyr(tBu)—OH and Boc-Asp(OtBu)—OH. When assembly of the peptide on the resin had terminated, the Dde protective group of the side chain of the Dap residue was removed by treating it with a 4% solution of hydrazine in DMF. Two successive 10-minute treatments were used for this deprotection reaction. Next, the cleavage reaction of the peptide partly protected by the resin was performed; the resin was placed on a porous septum and treated with an 0.5% solution in volume of TFA in dichloromethane for 3-5 minutes, the operation being repeated 10 times. The acid washing solution was collected in a flask containing 10% pyridine. After eliminating 90% of the starting solvent volume by evaporation at reduced pressure, the peptide was precipitated by addition of cold water and subsequently washed with water. After checking with Maldi mass spectroscopy for the presence of the peptide with all the protective groups except for the one on the Dap side chain (molecular weight 2320), the cyclisation reaction was performed. The C-terminal carboxyl group on the lysine residue formed an amide bond with the amino group in position 3 of 2,3-diaminopropionic acid. The reaction was carried out in DMF at a peptide concentration of $5.10^{-4}$ M by adding the carboxyl function activator HATU in excess of 4 equivalents and the DIEA base to a pH of 8.5. The mixture was kept under stirring for 5 hours at 40° C. The solvent was then removed under reduced pressure, and the protective groups on the side chain of the amino acids and on the carboxyl functions of the DTPA chelating agent were cleaved by the following procedure. The peptide compound was treated in a flask under stirring for 2 hours with a mixture of TFA containing EDT (2.5%), TIS (1%) and water (2.5%). The homogeneity of the crude product was checked by analytical HPLC; the crude product presented a main peak with a retention time of 16.3 minutes (column: reverse phase C18; eluents: water with 1% TFA and acetonitrile with 1% TFA; elution gradient: water percentage from 80% to 20% in 25 minutes). The product was purified by preparative HPLC, with the same separation method as used on an analytical scale. The purity of the product obtained exceeded 98%, as confirmed by analytical HPLC, with a yield exceeding 50% of the expected theoretical yield. The identity of the product was confirmed with Maldi mass spectroscopy, which showed the peak at the expected mass value: 1650.

EXAMPLE 5

Preparation of the indium complex with formula (XX)

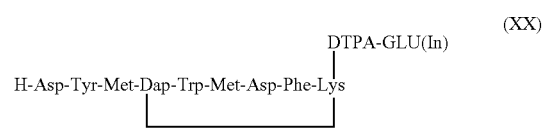

The compound of formula (XX) was synthesised by reacting the compound having formula (XIX), prepared as described in example 4, with indium trichloride. The indium salt (II) was dissolved in a solution of 3% citrate buffer in water, and the resulting solution was added to a solution containing the compound of formula (XX), 0.5 indium equivalents, in water at pH 7.8. After 24 hours the product was purified with HPLC and characterised with Maldi mass spectroscopy, which showed the peak at the expected mass value: 1762.

The invention claimed is:
1. A compound having the general formula (IX):

$$A\text{-}[Y]_z\text{---}C \qquad (IX)$$

wherein A is a peptide selected from:
H-Xaa1-Xaa2-Xaa3-Xaa4-Met-Dap-Trp-Met-Asp-Xaa10-Lys

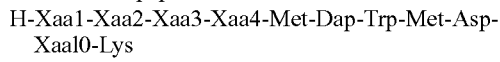

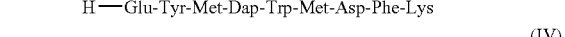

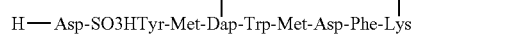

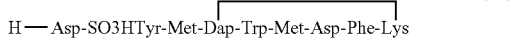

-continued

(VIII)

z is an integer between 0 and 5,

Y is a spacer chain bonded to one of the functionalities present on the side chains of the individual amino acids present in peptide A, or to an N-terminal (—NH$_2$) group or a C-terminal (—CO$_2$H) group of the peptide A, and to C; when z is an integer between 2 and 5, Y may be the same or different from each other, and C is a chelating agent bonded covalently to spacer chain Y or directly to peptide A, or to a number of amino acid units of peptide A, which is able to complex a paramagnetic metal or a radioisotope, their complexes with radioactive or paramagnetic metals or radioactive halogens, and salts thereof with physiologically acceptable organic or inorganic bases or with anions of physiologically acceptable organic or inorganic acids.

2. A compound as claimed in claim 1, wherein C is selected from the group consisting of: LDTA; DTPA; LOB-DTPA; BOPTA; DTPA-BMA; DTPA-GLU; DTPA-Lys; DOTA; DOTMA; DO3A; HPDO3A; MCTA; DPDP; LDTP; 1,4,7,10-tetraazacyclododecano-1,4,7,10 tetrakis[methylene(methylphosphonic)]acid; 1,4,7,10-tetraazaciclododecano-1,4,7,10-tetrakis[methylene(methylphosphonic)]acid; texaphyrines, porphyrins, phthalocyanines; compounds of formula (N amino/amido)$_{4-j}$ (S thiol)$_j$ (XIII), wherein j has an integer value of 0,1 or 2.

3. A compound as claimed in claim 1, wherein Y is a group of formula:

wherein r, 1, and q are each independently 0 or 1, and p can vary between 0 and 10, provided that at least one of 1, r and q is other than zero;

X is an O atom, or a —NR group wherein R is an H atom or an alkyl group (C$_1$-C$_5$);

K is a benzene ring, substituted or non-substituted, or a —CHR$_1$ group wherein
R$_1$ is a hydrogen atom or a —COOH or SO$_3$H group; and W is a —CO— or —CS— group.

4. A compound as claimed in claim 3 wherein spacer chain—[Y]$_z$—has the following formula (X):

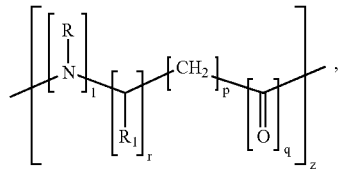

wherein z is an integer between 0 and 5; R is an H atom or an alkyl group (C$_1$-C$_5$) and R$_1$ is a hydrogen atom or a —COOH or —SO$_3$H group; r, 1, and q are each independently 0 or 1, and p can vary between 0 and 10, provided that at least one of 1, r and q is other than zero.

5. A compound as claimed in claim 4 wherein the spacer chain —[Y]$_z$—has the following formula (XI):

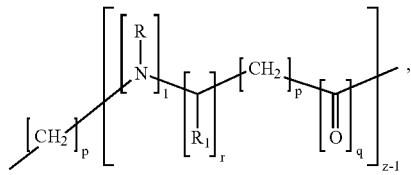

wherein z is an integer between 2 and 5; R is an H atom or an alkyl group(C$_1$-C$_5$) and R$_1$ is a hydrogen atom or a —COOH or —SO$_3$H group; r, 1, and q are each independently 0 or 1, and p can vary between 0 and 10, provided that at least one of 1, r and q is other than zero.

6. A compound as claimed in claim 3, in which the spacer chain —[Y]$_z$—has the following formula (XII):

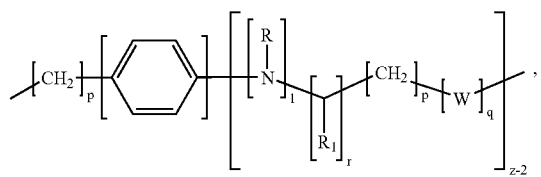

wherein z is an integer between 2 and 5; R is an H atom or an alkyl group (C$_1$-C$_5$) and R$_1$ is a hydrogen atom or a —OOH or SO$_3$H group; W is a —CO— or a —CS— group; r, 1, and q are each independently 0 or 1, and p can vary between 0 and 10, provided that at least one of 1, r and q is other than zero.

7. A compound as claimed in claim 1 wherein Y is one of the following groups: —(CH$_2$)$_2$—CO—, —(CH$_2$)$_4$NH—, —(CH$_2$)$_4$—NH—CO—(CH$_2$)$_2$—CO—, —CH$_2$—Ph—CH$_2$—CO—, —CH$_2$—Ph—NH—CS—.

8. A compound as claimed in claim 1, wherein C is DTPA, DTPA-Lys, or DTPA-GLU.

9. A compound as claimed in claim 1, wherein C is DOTA or DO3A.

10. A compound as claimed in claim 1, wherein said compound is a cholecystokinin agonist or antagonist.

11. A compound as claimed in claim 1 for the identification and localization of primary animal and human tumors and their metastases which over-express type A cholecystokinin receptors in higher quantities than in non-pathological situations.

12. A compound as claimed in claim 1 for the identification and localization of primary animal and human tumors and their metastases which over-express type B cholecystokinin receptors in higher quantities than in non-pathological situations.

13. A compound as claimed in claim 1 for the identification and localization of primary animal and human tumors and their metastases which over-express type A and/or B cholecystokinin receptors in higher quantities than in non-pathological situations.

14. A pharmaceutical, or diagnostic contrastographic or scintigraphic composition comprising a chelate as claimed in claim 1 or a salt thereof.

15. A diagnostic kit for the preparation of a radiopharmaceutical composition wherein said kit comprises an aseptically sealed vial containing a pre-determined amount of a compound as claimed in claim 1 and a sufficient quantity of reducing agent used to label the compound with technetium-99m, rhenium-186 or rhenium-188.

16. Diagnostic compositions for producing image organs and/or tissues and/or cells of the human or animal body by nuclear resonance or scintigraphy comprising a complex of a compound of claim 1 with one or more radioactive or paramagnetic metals or radioactive halogens.

17. A compound as claimed in claim 1 complexed with a bi-trivalent ion of one or more metal elements having atomic numbers ranging from 20 to 31, 39, 42-44, 49 or 57-83.

18. A compound as claimed in claim 1 complexed with one or more radioisotopes selected from $^{123}$I, $^{125}$I, $^{131}$, $^{74}$Br, $^{76}$Br, $^{75}$Br, $^{77}$Br, $^{82}$Br, $^{99m}$Tc, $^{203}$Pb, $^{67}$Ga, $^{68}$Ga, $^{72}$As, $^{111}$In, $^{113}$In, $^{90}$Y, $^{97}$Ru, $^{82m}$Rb, $^{62}$Cu, $^{64}$Cu, $^{52m}$Fe, $^{52}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{188}$Re, $^{186}$Re, $^{161}$Tb and $^{51}$Cr.

* * * * *

UNITED STATES PATENT AND TRADEMARK OFFICE
CERTIFICATE OF CORRECTION

PATENT NO. : 7,329,644 B2
APPLICATION NO. : 10/479096
DATED : February 12, 2008
INVENTOR(S) : Saviano et al.

It is certified that error appears in the above-identified patent and that said Letters Patent is hereby corrected as shown below:

In column 18, lines 53 and 54 should be deleted

In column 18, line 66, the penultimate amino acid of peptide (VI) "-Phe-" should read "-Val-"

In column 19, line 23, "LDTA" should read "EDTA"

In column 19, line 23, "LOB" should read "EOB"

In column 19, line 25, "LDTP" should read "EDTP"

In column 19, line 27, "methylphosphonic" should read "methylphosphinic"

In column 20, line 34, "-OOH" should read "-COOH"

In column 22, line 7, "$^{52}$Mn" should read "$^{52m}$Mn"

Signed and Sealed this

Twenty-eighth Day of July, 2009

JOHN DOLL
*Acting Director of the United States Patent and Trademark Office*